United States Patent
Ashmead et al.

(10) Patent No.: US 7,150,815 B2
(45) Date of Patent: Dec. 19, 2006

(54) POLYMERIC MICROFABRICATED FLUIDIC DEVICE SUITABLE FOR ULTRAVIOLET DETECTION

(75) Inventors: James William Ashmead, Middletown, DE (US); Sau Lan Tang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 626 days.

(21) Appl. No.: 10/380,608

(22) PCT Filed: Oct. 3, 2001

(86) PCT No.: PCT/US01/30974

§ 371 (c)(1),
(2), (4) Date: Mar. 13, 2003

(87) PCT Pub. No.: WO02/29397

PCT Pub. Date: Apr. 11, 2002

(65) Prior Publication Data

US 2004/0084402 A1 May 6, 2004

Related U.S. Application Data

(60) Provisional application No. 60/238,066, filed on Oct. 5, 2000, provisional application No. 60/238,067, filed on Oct. 5, 2000.

(51) Int. Cl.
*G01N 27/453* (2006.01)
(52) U.S. Cl. ..................... 204/601; 204/600
(58) Field of Classification Search ........ 204/450–455, 204/600–605
See application file for complete search history.

(56) References Cited

U.S. PATENT DOCUMENTS

| 4,908,112 | A | | 3/1990 | Pace |
| 5,017,540 | A | * | 5/1991 | Sandoval et al. ........... 502/158 |
| 5,126,022 | A | | 6/1992 | Soane et al. |
| 5,334,424 | A | * | 8/1994 | Hani et al. .................. 428/1.6 |
| 5,444,807 | A | * | 8/1995 | Liu ............................ 385/125 |
| 5,637,469 | A | | 6/1997 | Wilding et al. |
| 5,858,188 | A | | 1/1999 | Soane et al. |
| 5,885,470 | A | | 3/1999 | Parce et al. |
| 5,965,410 | A | * | 10/1999 | Chow et al. ................ 435/91.2 |
| 6,107,038 | A | * | 8/2000 | Choudhary et al. ............ 435/6 |
| 6,372,353 | B1 | * | 4/2002 | Karger et al. ................ 428/447 |
| 6,542,231 | B1 | * | 4/2003 | Garrett ....................... 356/246 |
| 6,787,016 | B1 | * | 9/2004 | Tan et al. .................... 204/455 |

FOREIGN PATENT DOCUMENTS

EP    0386925    9/1990

(Continued)

OTHER PUBLICATIONS ("Topasâ Cyclic Olefin Copolymer: The Benefits are Clear," Ticona Automotive—Automotive Systems—Profile vol. 1, issue 6, published 2004, only 1 page long).*

(Continued)

*Primary Examiner*—Alex Noguerola

(57) ABSTRACT

A polymer-based microfluidic device and its manufacturing methods. This microfluidic device is suitable for chromatographic and electrophoretic separations in which the detection of the components in the fluid is by means of ultraviolet (UV) spectroscopy. The device further comprises at least one cooling channel adjacent the separation channel, said cooling channel conducting a cooling fluid through the device for removing heat from the the separation channel. At least one section of the separation channel has an increased cross-sectional dimension with respect to other sections of said channel to provide an increased optical path length when the device is used in an ultraviolet detection arrangement.

1 Claim, 2 Drawing Sheets

FOREIGN PATENT DOCUMENTS

| | | |
|---|---|---|
| EP | 0523680 | 1/1993 |
| JP | 09-304338 A * | 11/1997 |
| WO | WO 98/46438 | 10/1998 |
| WO | WO 99/12016 | 3/1999 |
| WO | WO 99/49319 | 9/1999 |
| WO | WO 00/56808 | 9/2000 |

OTHER PUBLICATIONS

"Your Clear Advantage: Topas COC—A clearly extraordinary polymer," downloaded Mar. 6, 2006 from www.topas.com/products-topas_coc.*

Zimmermann et al. ("Electrokinetic Measurements Reveal Interfacial Charge at Polymer Films Caused by Simple Electrolyte Ions," J. Phys. Chem. B 2001, 105, 8544-8549).*

JPO English language translation of JP 09-304338 A (Iwata Yousuke) Nov. 28, 1997.*

PCT/US01/30974, International Search Report dated Sep. 10, 2002.

James W. Jorgenson and Krynn DeArman Lukacs, High-Resolution Separations Based on Electrophoresis, Journal of Chromatography, 218 (1981) 209-216.

Zhonghui H. Fan and D. Jed Harrison, Micromachining of Capillary Electrophoresis Injectors and Separators on Glass Chips and Evaluation of Flow at Capillary Intersection, Anal. Chem. 1994, 66, 177-184.

Adam T. Woolley, George F. Sensabaugh and Richard A. Mathies, High-Speed DNA Genotyping using Microfabricated Capillary Array Electrophoresis Chips, Anal. Chem. 1997, 69, 2181-2186.

Randy M. McCormick, Robert J. Nelson, M. Goretty Alonso-Amigo, Dominic J. Benvegnu and Herbert H. Hooper, Microchannel Electrophoretic Separations of DNA in Injection-Molded Plastic Substrates, Anal. Chem. 1997, 69, 2626-2630.

Hou-pu Chou, Charles Spence, Ann Fu, Axel Scherer and Stephen Quake, Disposable Microdevices for DNA Analysis and Cell Sorting, Solid-Stateسensor and Actuator Workshop Proceedings, Jun. 1998, pp. 11-14.

Carlo S. Effenhauser, Gerard J. Bruin, Aran Paulus and Markus Ehrat, Integrated Capillary Electrophoresis on Flexible Silicone Microdevices: Anaylsis of DNA Restriction Fragments and Detection of Single DNA Molecules on Microchips, Anal. Chem. 1997, 69, 3451-3457.

Travis D. Boone, Herbert H. Hooper and David S. Soane, Integrated Chemical Analysis on Plastic Microfluidic Devices, Solid-State Sensor and Actuator Workshop Proceedings, Jun. 1998, pp. 87-92.

Matthew A. Roberts, Joel S. Rossier, Paul Bercier and Hubert Girault, UV Laser Machined Polymer Substrates for the Development of Microdiagnostic Systems, Anal. Chem. 1997, 69, 2035-2042.

Eric T. Lagally, Brian M. Paegel and Richard A. Mathies, Microfabrication Technology for Chemical and Biochemical Microprocessors, Micro Total Analysis Systems 2000 Symposium, pp. 217-220.

Ann Eckerson et al., High-Throughput SNP Scoring in a Disposable Microfabricated CD Device, Micro Total Analysis Systems 200 Symposium, pp. 521-524.

G. Weber, M. Johnck, D. Siepe, A. Neyer and R. Hergenroder, Capillary Electrophoresis with Direct and Contactless Conductivity Detection on a Polymer Microchip, Micro Total Analysis Systems 2000 Symposium, pp. 383-386.

Tasso Miliotis, David Ericsson, Gyorgy Marko-Varga, Simon Ekstrom, Johan Nilsson and Thomas Laurell, Interfacing Protein and Peptide Separation to Maldi-Tof MS using Microdispensing and On-Target Enrichment Stratgies, Micro Total Analysis Systems 2000 Symposium, pp. 387-390.

T. Nishimoto, Y. Fujiyama, H. Abe, M. Kanai, H. Nakanishi and A. Aral, Microfabricated CE Chips with Optical Slit for UV Absorption Detection, Micro Toal Analysis Systems 2000 Symposium, pp. 395-398.

Rebecca J. Jackman, Tamara M. Floyd, Martin A. Schmidt and Klavs F. Jensen, Development of Methods for On-line Chemical Detection with Liquid-Phase Microchemical Reactors using Conventional and Unconventional Techniques, Micro Total Analysis Systems 2000 Symposium, pp. 155-158.

H. Bjorkman, C. Ericson, S. Hjerten and K. Hjort, Diamond Microchip Capillary Chromatography of Proteins, Micro Total Analysis Systems 2000 Symposium, pp. 187-190.

* cited by examiner

POLYMERIC MICROFABRICATED FLUIDIC DEVICE SUITABLE FOR ULTRAVIOLET DETECTION

This application claims the benefit of priority of International Application No. PCT/US01/30974, filed Oct. 3, 2001, which in turn claims benefit of priority of U.S. Provisional Application 60/238,066, filed Oct. 5, 2000 and U.S. Provisional Application 60/238,067, filed Oct. 5, 2000.

FIELD OF THE INVENTION

This invention relates to a polymer-based microfluidic device and its manufacturing methods. This microfluidic device is suitable for chromatographic and electrophoretic separations in which the detection of the components in the fluid is by means of ultraviolet (UV) spectroscopy and for chromatographic and electrophoretic separations in which the detection of the components in the fluid is by means of visible light, fluorescence, chemiluminescence or scattering or by means of electrochemical and electroconductivity detection.

TECHNICAL BACKGROUND OF THE INVENTION

There is a large volume of literature on the manufacturing of planar microfabricated devices primarily using electroosmotic, electrokinetic, and/or pressure-driven motions of liquid and particles as the means of fluid transport. Microfluidic devices are considered an enabling technology for low cost, high versatility operations, many of which find great utility in the biotechnology and pharmaceutical industries. Jorgenson et al., Journal of Chromatography, vol. 218, 1981, pp. 209–214 and U.S. Pat. No. 4,908,112 teach the use of microfluidic devices made of silicon having a glass cover to perform separation operations using capillary electrophoresis (CE), a common application for such a device. Their application was the electrophoretic separation of double-stranded DNA fragments labeled with intercolating dye for fluorescence detection. It is known that silicon has limitations for this application because the electric field needed to drive the fluid in a capillary electrophoretic separation device often exceeds the dielectric breakdown field of silicon. U.S. Pat. No. 5,126,022 and U.S. Pat. No. 5,858,188 are exemplary of the use of insulating substrates for light or laser induced fluorescence (LIF) detection systems. Polymeric materials, in particular poly methyl methacrylate (PMMA), have the optical clarity in the visible wavelengths required for such LIF detection systems. It has been demonstrated that PMMA can be injection molded to reproduce features of about 100 μm, a dimension usable in the construction of microfluidic channels in these devices. However, injection molding at dimensions smaller than 100 μm has not been disclosed. These smaller dimensions are especially desirable for capillary electrophoretic separations. These smaller dimensions minimize the spatial spread of the sample plug in sample inlet channels. U.S. Pat. No. 5,885,470, and subsequent patents with the same assignees, disclose polymer devices made of polydimethylsiloxane (PDMS), PMMA, polyurethane, polysulfone and polytetrafluoroethylene (PTFE), polyvinyl chloride (PVC) and polycarbonate. Each of these polymers suffers disadvantages. All these materials are hydrophobic. PDMS and polyurethane are not injection moldable, PVC is typically chemically impure, PMMA and polycarbonate are not UV-transparent and PTFE is typically not optically clear.

The proceedings of the Micro Total Analysis Systems-2000 Symposium, A. Van Den Berg and W. Olthuis, ed., Kluwer Academic Publishers, Dortrecht, 2000, exemplify the progress made in this field, in device fabrication methods, complexity and applications. Microfluidic devices made of glass are exemplified by Zhonghui H. Fan and D. Jed Harrison, Analytical Chemistry, vol. 66, 1994, pp. 177–184 and A. M. Woolley et al., Analytical Chemistry, vol. 69, 1997, pp. 2181–2186. Microfluidic devices made of polymeric substrates are exemplified by R. M. McCormick et al., Analytical Chemistry, vol. 69, 1997, pp. 2626–2630, Hou-pu Chou et al., Solid-State Sensor and Actuator Workshop Proceedings, June 1998, pp. 11–14, C. S. Effenhauser et al. Analytical Chemistry, vol. 69 (1997) 3451–3457, T. D. Boone et al., Solid-State Sensor and Actuator Workshop Proceedings, June 1998, pp. 87–92, and M. A. Roberts et al., Analytical Chemistry, vol. 69, 1997, pp. 2035–2042.

A large fraction of the applications using these devices have been in DNA analysis with fluorescence detection. E. C. Lagally et al., Micro Total Analysis Systems-2000 Symposium, pp. 217–220, discusses high throughput DNA analysis with integrated PCR. C. S. Effenhauser, ibid., discusses DNA restriction enzymes. A. Eckersten el al., Micro Total Analysis Systems-2000 Symposium, pp. 521–524, discusses high throughput single nucleotide polymorphism (SNP) scoring in a disposable microfabricated capillary electrophoresis (CE) device. Other applications include chemiluminescence, electroconductivity and mass spectrometry detection. U.S. Pat. No. 5,637,469 (Wilding et al) teaches sperm sample analysis with chemiluminescence detection. G. Weber et al., Micro Total Analysis Systems-2000 Symposium, pp. 383–386, discusses organic acid separation and detection using electroconductivity detection. T. Miliotis, Micro Total Analysis Systems-2000 Symposium, pp. 387–390, discusses protein and peptide separation using mass spectrometry detection. Commercial systems for microfluidic applications to DNA analysis have also started to appear on the market.

Fluorescence detection, or laser-induced fluorescence (LIF), is a very sensitive detection technique, but it requires that analytes be derivatized with fluorescent dyes. The method has wide applications in DNA analysis in which dye derivatization is standard procedure. On the other hand, UV spectrophotometry as a detection technique is attractive because many analytes of interest are UV chromophores and therefore do not require sample preparation procedures such as tagging analytes with fluorophores. Moreover, UV spectroscopy, being an optical technique, is more robust than techniques such as electroconductivity.

Electroconductivity detection is susceptible to contamination problems on the electrode and is difficult to operate in capillary electrophoresis because of the presence of the high electrophoretic voltage in the background. For this reason, UV detection has a far wider range of applications including the analyses of proteins, small molecules, chiral compounds, etc. The most common substrate material for microstructure fabrication has been Pyrex®, which is not particularly transparent at wavelengths shorter than four hundred nanometers (400 nm). The use of Pyrex® in microfluidic devices has hindered the application of these devices to UV spectroscopy. Likewise, the most popular polymer resins, such as PMMA, used in visible wavelength optical applications are not particularly transparent below three hundred nanometers (300 nm). The transparent polymers in the previously mentioned U.S. Pat. No. 5,885,470 are not UV-transparent except PDMS, which is not injection moldable.

The other hindrance for incorporating UV spectrophotometry as the detection technique is that UV sensitivity is several orders of magnitude lower than that of light fluorescence spectroscopy. Quartz, a material that has been used in conventional chromatography and capillary electrophoresis, requires very high temperatures to bond a cover to a surface having microfabricated structures. There have been some recent efforts to circumvent this problem. T. Nishimoto et al., Micro Total Analysis Systems-2000 Symposium, pp. 395–398, describes a special HF bonding method that allows easier bonding, and the incorporation of a silicon slit in the detection window to cut down background stray light to increase signal to noise intensity. R. J. Jackman, Micro Total Analysis Systems-2000 Symposium, pp. 155–158, has adopted another strategy, the use a layer of photoresist as bonding agent. Still another strategy, disclosed by H. Bjorkman et al., Micro Total Analysis Systems-2000 Symposium, pp. 187–190, uses artificial diamond as the optical window material. Artificial diamond, however, is made by an expensive process.

The scientific literature has been somewhat vague concerning specific methods to seal channels in polymer devices. A common way to seal microfluidic channels in polymer substrates is to simply cover the channels with an adhesive covered tape having low background fluorescence at visible wavelength. The tape is typically bonded to the substrate using UV bonding or similar techniques known in the art. The tape is not an optimal solution for sealing devices because it has limited mechanical strength, and is generally not UV-transparent.

Although prior art polymeric materials suffer certain deficiencies, they are becoming an increasingly popular choice for fabricating microfluidic devices. Prior art polymeric materials are not sufficiently transparent in the ultraviolet. Polymeric materials suffer from the deficiency of lower thermal conductivity than silicon and glass, the original materials of construction for microfluidic devices. A common need for all analytical devices, particularly devices employing ultraviolet detection, is increased sensitivity. The present invention overcomes these deficiencies.

SUMMARY OF THE INVENTION

Disclosed is an improved microfluidic system, comprising a microfluidic device which comprises a planar substrate having a first surface and a planar cover having a first surface, the first surface of the cover being bonded to the first surface of the planar substrate, at least one of the substrate or cover being substantially fabricated from a polymeric material, the device having at least first and second intersecting channels disposed therein at the interface of the bonded surfaces, the channels having interior surfaces being optionally wetted with aqueous and/or organic/aqueous buffers, and having a zeta potential associated therewith, which zeta potential is capable of supporting an electroosmotic mobility of a fluid in said channels of at least $1 \times 10^{-5}$ $cm^2V^{-1}s^{-1}$, wherein said fluid is a sodium borate buffer having an ionic strength of between about 1 and about 50 millimoles (mM), and a pH of from about 7 to about 9.5, at least one of said at least first and second intersecting channels having at least one cross-sectional dimension in the range of from about 0.1 micrometer to about 1000 micrometer;

at least first, second and third ports disposed at termini of said first channel and at least one terminus of said second channel, whereby said ports are in electrical contact with the fluid in said first and second channels; and an electrical control system for concomitantly applying a voltage at least two of said at least first, second and third ports, to selectively direct flow of the fluid in said first and second intersecting channels by electroosmotic flow, wherein the improvement comprises the polymeric material being either a cycloolefin copolymer or an amorphous fluoropolymer. Preferably a fluoropolymer known as Teflon AF® is used.

The interior surface of said channels may be further modified by surface modification chemistry to achieve a different zeta potential, which is capable of supporting electroosmotic mobility of a fluid in said channels of up to $7 \times 10-4$ $cm^2V^{-1}s^{-1}$.

The improvement also comprises inexpensive injection molding methods for the manufacturing of the microfluidic devices made of the said cycloolefin copolymer, and a thermal/pressure method for bonding the said planar surfaces to form the enclosed channels.

The improvement also comprises a means of rendering the Teflon AF® surface hydrophilic and a means for bonding the two said planar substrates for fluidic transport. The improvement also enables the microfluidic devices to be used when ultraviolet spectrophotometry is used for detecting analytes moving through the channels.

Further disclosed is a substantially polymeric microfluidic device comprising a body having at least one cooling channel distinct from any reagent bearing channel, the cooling channel for passing a cooling fluid through the microfluidic device to remove heat from the reagent bearing channel to control the temperature of the reagent.

Further disclosed is a substantially polymeric microfluidic device comprising a body having a reagent-bearing channel, at least one section of which has an increased cross-section dimension with respect to other sections of said reagent-bearing channel. This increased dimension provides an increased optical path length through the reagent for the purpose of increasing the sensitivity of any optical based analysis conducted on the reagent in the channel.

Further disclosed is a substantially polymeric microfluidic device comprising a body which combines the features of a cooling channel and a reagent-bearing channel, at least one section of which has an increased cross-section dimension with respect to other sections of said reagent-bearing channel.

In one embodiment of the microfluidic device, at least one section of one of the at least first and second intersecting channels has an increased cross sectional dimension with respect to other sections of said channel, to provide an increased optical path length when used in an ultraviolet detection arrangement.

DETAILED DESCRIPTION OF THE INVENTION

Figure 1:
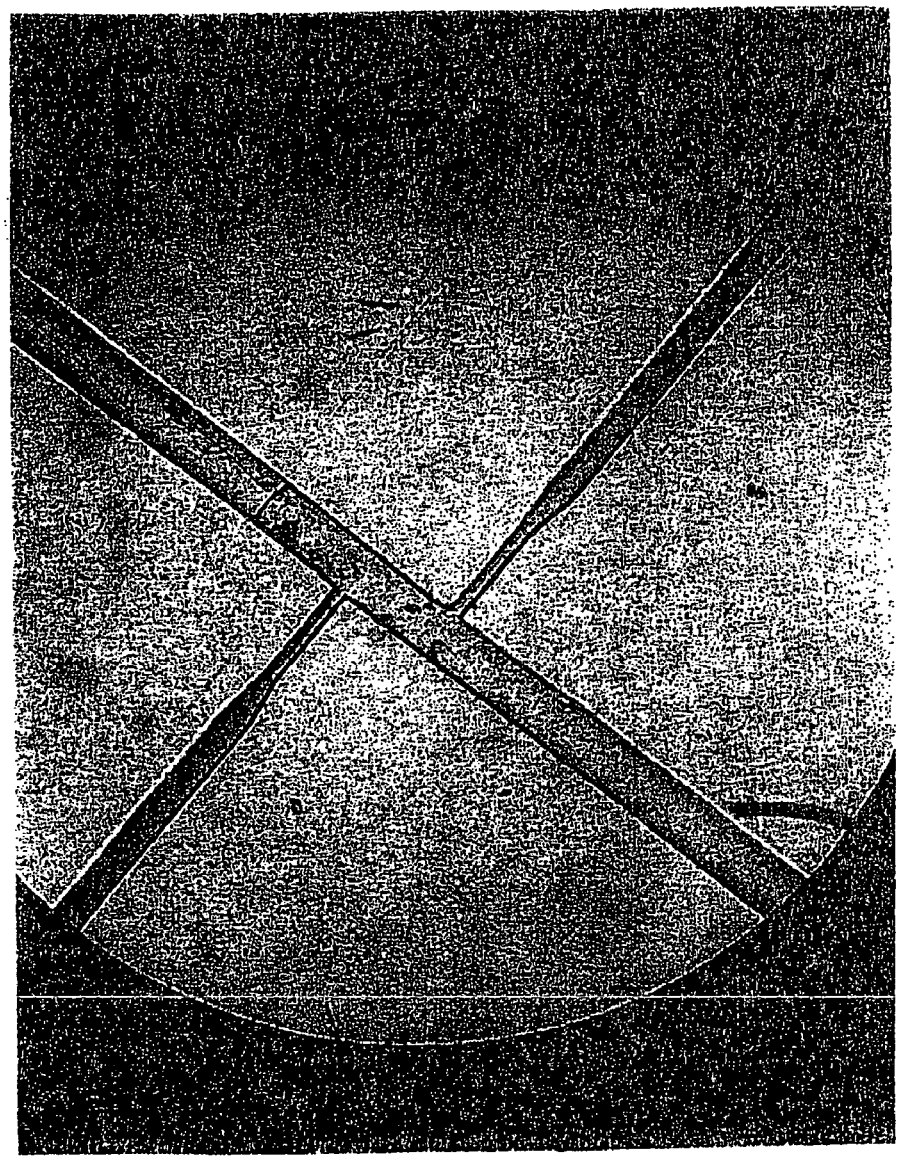
FIG. 1 is a photograph of a polymeric microfluidic device comprising a separation channel and two injection channels.

This invention discloses the use of a polymer resin that is substantially transparent at ultraviolet wavelengths, i.e., greater than fifty percent (50%) at wavelengths two hundred fifty nanometers or longer (>250 nm), and that is transparent and has a low fluorescence background at visible wavelengths. For example, fluorescence background when using 488 nm light as excitation source is negligible, thus enabling efficient LIF detection.

In one embodiment, this polymeric resin used is an inexpensive (a few dollars a pound) copolymer of ethylene and norbornene with the trade name of Topas®. This resin does not contain double bonds, or any chemical atoms other than carbon and hydrogen. Chemically it is different from all prior art compounds. Because of this chemical composition it transmits UV at >50% efficiency above 250 nm. It is also relatively chemically pure (no leaching of polymer additives). It can also be plasma-treated to wet aqueous buffers completely. This resin is injection moldable to reproduce features as small as 20 μm wide and 12 μm deep. The microchannels thus produced can be sealed with another piece of polymer resin with or without another layer of polymer as a "glue".

Another embodiment of the invention describes a polymeric microfluidic device that can be used in conjunction with optical detection techniques with the wavelength range from 200 nm to the infrared. The microfluidic device is made of Teflon AF® amorphous fluoropolymer. Teflon AF® amorphous fluoropolymer is inherently hydrophobic and does not bond easily to any material. To overcome these problems, which would prevent this material from being used in microfluidic applications, a layer of polyvinyl alcohol (5% PVA in water) is spin-coated onto the surface of the Teflon AF® amorphous fluoropolymer film to be used as the cover. Microfluidic features are fabricated into Teflon AF® amorphous fluoropolymer by compression molding or hot embossing with a master of negative features as known in the art. The Teflon AF® amorphous fluoropolymer film with the PVA coating is then placed on top of the Teflon AF® amorphous fluoropolymer side with the microfabricated features with the PVA coating being sandwiched by the two amorphous fluoropolymer films. The sandwiched structure is then placed in a hydraulic press at 75° C. and 500–1000 pounds per square inch (psi). The resulted structure transmits light at wavelengths greater than 200 nm with better than 50% efficiency. The microfluidic device thus made may be used for analyzing a large variety of materials including, but not limited to, proteins and peptides, organic compounds, labeled DNA fragments and SNP's.

This invention comprises polymer microfluidic devices with micron-scale features obtained through conventional injection molding technology. These features are exemplified as channels from 20 μm to 200 μm wide, 10 μm to 100 μm deep on the surface of the polymer substrate 0.5 mm to 2 mm thick which transmits at least 10% of the incident photons in the wavelength range of 240 to 350 nm. The microfluidic channels are sealed by a cover that also transmits UV light.

Preferably, the polymer resin is a saturated co-polymer comprising polyethylene and polycyclic olefins such as norbornene. An example of such a resin is Topas® cyclic olefin copolymer, available from the Ticona division of Celanese AG. The grade of Topas® cyclic olefin copolymer most preferred for this invention is Topas® 8007. Preferred injection molding thermal conditions for the Topas® 8007 grade are 160° C. –200° C. for resin and nozzle, 60° C. for the mold. The injection molded pieces with or without microfluidic structures are plasma treated to improve wetting properties with aqueous buffers. The plasma-treated surfaces of the injection-molded pieces may be further rinsed with surface treatment solutions such as octyltriethoxysilane to produce a surface that may become charged when a polar buffer solution is used.

After surface treatment, the microfluidic channels are sealed by any of the following methods. In a first method, an injection-molded plaque of Topas® 8007 with or without microfluidic structures is placed on top of the plaque with the microfluidic channels. The two pieces are subjected to 500 to 1000 psi of pressure at 75° C. for, at most, several minutes. The two pieces are allowed to cool to about at least about 60° C. before the pressure is released. This results in a fluid-tight bond between the two plaques.

In a second method, an injection-molded plaque of Topas® 8007 with or without microfluidic stuctures is placed on a spin-coater and a layer of polyvinyl alcohol (PVA) is spin-coated onto the plaque. At a 1000 rpm, the resulted PVA layer is still "wet" at the end of the spin-coating process. Another injection-molded plaque with or without PVA coating is then put on the wet PVA layer and a gentle pressure is applied. When the PVA layer has dried, the two plaques are bonded together with the pressure/thermal process described above. Care must be taken to prevent PVA from getting inside the microfluidic channel.

When an amorphous fluoropolymer known as Teflon AF® is utilized as the polymer, a microfluidic device better than 50% transparent at UV wavelengths longer than 200 nm may be produced. Such a device specifically comprises: a substantially planar film of Teflon AF® amorphous fluoropolymer made from compression molding at 230° C. and 1000–20000 psi. The lower range of the pressure is used if the molding master contains microfabricated features 20–1000 μm in width and 10–40 μm in depth. The higher range of the pressure is used if the Teflon AF® amorphous fluoropolymer film made does not contain microfabricated features. Alternatively, a layer of PVA is spin-coated onto the side of the Teflon AF® amorphous fluoropolymer film without microfabricated structures by using an about 5% PVA in water solution. PVA wets the Teflon AF® film surface. The side of the Teflon AF® film with the microfabricated features is placed against the side of the Teflon AF® film with the PVA coating and the sandwiched structure is placed in a press at 75–80° C. at 500–1000 psi for several minutes. The resulting microfluidic device transmits UV above 210 nm at more than 50% efficiency.

The devices disclosed here are useful as inexpensively manufactured devices that can be used for large range of "Lab-on-a-chip" applications using both UV and LIF as detection techniques, or devices that have exceptional UV transmission characteristics.

The microfluidic device of the present invention is depicted in FIG. 1. In this injection-molded device, the separation channel 10 is one hundred micrometers (100 μm) wide. Each of the two injection channels 20, 30 is fifty micrometers (50 μm) wide at the outer boundaries of the figure, necking down to twenty micrometers (20 μm) wide where they intersect the separation channel. In all channels, the depth is about fifteen micrometers (15 μm).

In bench-top capillary electrophoresis instruments, efficient cooling of the capillary during separation is critical to the quality of the results obtained: the reproducibility of both peak areas and retention times are affected. In severe situations, inadequate cooling can halt the separation because of gas bubble generation that accompanies higher temperatures. In bench-scale apparatus liquid immersion cooling of the capillary, typically using ethylene glycol, and sometimes, pressured gas or air draft cooling, is employed. As is expected, immersion cooling is more effective than air-cooling due to higher heat capacity of the liquid and the resulting increased heat transfer rate. Improved cooling leads to improved analytical results, especially true in separations using high current, i.e., greater than eighty microamperes (80 μA) and high salt content in the buffer, where Joule heating effect ($I^2R$ heat) is considerable.

In microfabricated capillary electrophoresis devices, Joule heating effects have heretofore been considered less severe because most microfabricated capillary electrophoresis channels have been made in glass or silicon substrates, which are relatively good thermal conductors. The bulk of glass or silicon surrounding the channel dissipates the heat generated adequately. Moreover, microfabricated channels typically have trapezoidal cross-section (wide and shallow) which contain a smaller current than a cylindrical silica tube of the same diameter. For these reasons, it is considered not necessary to actively cool the separation channel in microchannels in glass or silicon. As the trend to use polymer substrates grows, the joule heating effect has a larger impact on the quality of the separation since polymer substrates in general are poor thermal conductors compared to glass. This is especially true in devices with a high density of channels, as in high throughput screening CE devices.

Figure 2:
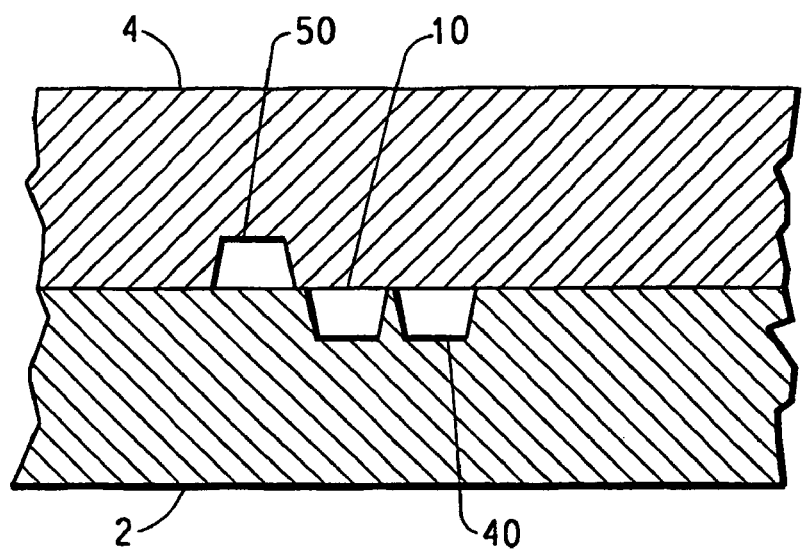
FIG. 2 is a sectional view, taken across the separation channel of a polymeric microfluidic device showing the reagent-bearing separation channel and two adjacent cooling channels.

A first cooling embodiment is shown in FIG. 2. As may be seen in this sectional view, showing a cross section of the separation channel 10 formed by the substrate 2 and the cover 4, one or more cooling channels 40 in the substrate 2, may be provided alongside the separation channel 10. A cooling agent, forced air or liquid coolant, can be circulated through channels 40 in close proximity of the source of the heat, i.e., the electrolyte fluid in the channels. The close proximity of the cooling channels 40 to the separation channel 10 is an efficient way to overcome the thermal conductivity deficiency of polymeric materials. In another embodiment, the cooling channels can be made on the cover plate as well as in the same substrate as the separation channel, as shown by cooling channel 50. In a third embodiment, a specially constructed cooling channel-containing cover plate can be employed with a conventional, non-cooling substrate containing a microfluidic device.

A major challenge for capillary electrophoresis as a preferred analytical technique is sensitivity enhancement. The preeminent detection mode in capillary electrophoresis is UV detection. One effective way to improve UV detection sensitivity in capillary electrophoresis is to lengthen the optical path of the UV light in the detection region. In benchtop capillary electrophoresis instruments using silica as the capillary, this strategy has been successful. The so-called "Z-cell", developed by LP Packings, the "bubble cell" and "high sensitivity cell" commercialized by Hewlett Packard, are examples of successful implementation of this strategy in macro scale instrumentation In the Z-cell device the separation channel has a first section on a first face of the substrate, a second section through the substrate, and a third section on the second face of the substrate. The optical detection path passes through the second section of the separation channel, i.e., through the thickness of the substrate. Although the "through device" optical path lengthens the optical path, the length is practically restricted to the thickness of the substrate. The z-cell requires channels fabricated on both surfaces of a substrate and "through substrate" drilling, operations which increase the cost of the device.

The device of the present invention provides a signal enhancement equivalent to the signal enhancement of the z-cell device. As may be seen in FIG. 3, a sectional view along the separation channel 10, the present device has the entire separation channel 10 on one face of the substrate 2, while increasing the optical path length on the same surface of the separation channel. The present arrangement is thought to be more desirable since it facilitates fabrication and offers flexibility in varying the path length to optimize the detection.

Figure 3:
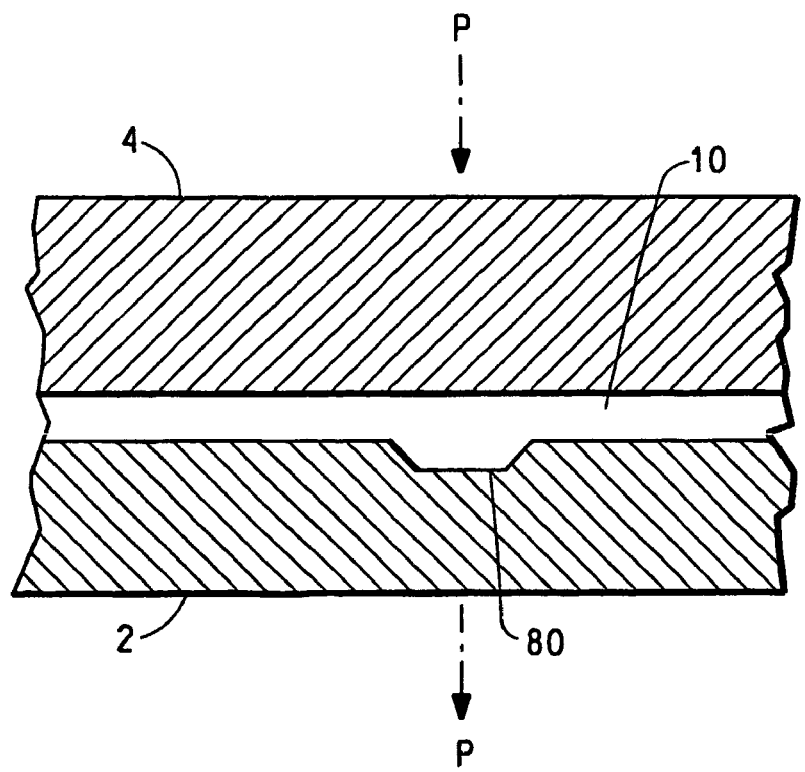
FIG. 3 is a sectional view, taken along the separation channel, showing a section of the separation channel having an increased vertical dimension.

The device of the present invention comprises a microfabricated channel 10 having an optical detection section 80 of the channel having an increased vertical dimension. The increased path length of optical path P increases the cross-section of analyte passing through the detection region to thereby increase the sensitivity of UV absorption. As shown in FIG. 3, this increased optical path length is about twice the normal depth of the channel 10. Further increases in the vertical dimension of the detection section can increase UV sensitivity of the device to approximately that obtained in conventional capillary electrophoresis. This translates to about micromolar sensitivity for para-hydroxycinnamic acid. The increased sensitivity is especially valuable in UV spectrophotometry.

EXAMPLES

Example 1

A three-inch diameter silicon negative master mold insert was fabricated using well-known procedures in the art. This silicon master had 3 separate microfluidic devices on the wafer. Each microfluidic device consisted of a 100-μm wide separation channel and two T-injection junctions. The injection channel was 50 μm wide at the end joining the injection well, and it narrowed down to 20 μm at the junction with the separation channel. This mold insert was attached onto the mold in the injection mold cavity with a double-sided adhesive tape. The injection molder was the horizontal type where the mold is positioned vertically with respect to the motion of the chuck holding the nozzle of the injection molder. In a vertical injection molder, the double-sided tape would not be needed.

The surface of the mold cavity was heated to about 60° C. Topas® 8007 pellets were outgassed overnight in a vacuum oven at a temperature no greater than 50° C. The resin temperature and nozzle temperatures were set at about 180° C., a temperature about 20° C. above the temperature recommended by the vendor. It was determined that this elevated temperature improved flow viscosity of the resin and resulted in optically clearer plaques. The mold cavity was such that a molded part, called a plaque, about 3 to 4 millimeters thick (about ⅛ inch) and the microfabricated features are reproduced in the plaque with high fidelity.

FIG. 1 shows two T-injection junctions, typical of these features under an optical microscope. The profile of the 100 μm wide separation channel was measured with with a profilometer. The depth of the channel was measured to be 12 μm+/−0.2 μm deep. The measured profile demonstrated that that the injection molding process exhibits sub-micron accuracy. The 20 μm wide channels were also reproduced with similar accuracy. The precision and accuracy of these profiles were identical to those obtained from the silicon master mold insert itself. A blank plaque without microfabricated features was likewise injection molded. Another grade resin, Topas® 5013 was also used. The flow viscosity of this resin was higher than that of 8007, resulting in visible flow lines in the finished plaques using the same injection molding conditions described above.

The plaques, with and without microfabricated features, were plasma treated with a hand-held plasma generator under the following conditions: 250 psi air, 1–2 inches above plaque, and 5–10 passes across the plaque with the hand-held plasma generator. Alternatively, water-saturated air was used, at a pressure of 122 psi, with all other conditions held constant.

After plasma treatment, the surface of the Topas® plaque was found to wet water completely. UV transmission scans were carried out on these plaques. The transmisson spectrum of the three millimeter (⅛") thick plaque over the range of 200 nm to 800 nm was measured to confirm its UV-transparency. Background fluorescence scans were also carried out using 488 nm light as the excitation source. Fluorescence was found to be negligible.

To seal the microfabricated features which were open channels on one face of the Topas® plaque, the following two procedures were carried out. In a first bonding procedure, the plasma-treated surfaces from the two Topas® plaques were placed against each other and placed in a press maintained at 75° C. A pressure of 500–1000 psi was applied for 15 minutes at 75° C. The plaques were then cooled in the press to about 60° C. and then the pressure was released. When the plaques were removed from the press they were found to be bonded together, i.e., they could not be taken apart without force.

In a second bonding procedure, the plasma-treated side of the blank Topas® plaque was first covered with a layer of PVA spin-coated on at 5000 rpm for 1 minute. The PVA-coated side of the blank plaque was placed against the plasma-treated side of another Topas® plaque having molded features and the sandwiched structure was placed in a press held at 75° C. A pressure of 500–1000 psi was applied for 15 minutes. The plaques were then cooled in the press to about 60° C. and then the pressure was released. When the plaques were removed from the press they were found to be bonded together, i.e., they could not be taken apart without force.

Example 2

A nickel mold was fabricated by electroplating a silicon positive having the microfabricated features with nickel. The resulted nickel mold was placed on the lower plate of a press. A ~2.5" diameter circular hole was cut out from a 0.004" thick Kapton® polyimide film. The resulted circular space was placed on the nickel mold so that the microfabricated features on the nickel mold were contained inside the circular space. The temperature of the press was maintained at about 230° C. Teflon AF® granules were placed inside the circular space to slightly over-fill the circular space. Another sheet of Kapton® was placed onto the surface of the Teflon AF® granules. A copper disk slightly larger than the circle was placed on the Kapton® sheet. The press was closed and the pressure was was applied gradually over a few minutes and the pressure was maintained at 1500 psi for 5–6 minutes. The resulting film of Teflon AF® was optically very clear and the microfabricated features were transferred from the nickel mold onto the film. A blank film of Teflon AF® was also compression molded in a similar fashion. For the blank film no nickel mold was needed. For the blank film the pressure was increased to 10,000 psi at 230° C. for 5 minutes.

The resulting Teflon AF® films were hydrophobic even after plasma treatment, as described in Example 1. To render the Teflon AF® film hydrophilic and still retain the optical property, a layer of PVA (5% PVA with molecular weight ~100,000 in de-ionized water) was spin-coated at 1000–5000 rpm onto one face of the blank Teflon AF® film. Surprisingly, PVA was found to adhere to Teflon AF® even without plasma-treatment. When the PVA film was dried, the side of the film with the PVA coating on was placed in contact with the face of the Teflon AF® film having the microfabricated features. The sandwiched structure was placed in a press between two Kapton® sheets and held at 75° C. –80° C. for 4 minutes at 500–1000 psi. The two Teflon AF® films adhered. The PVA coating was used as an aqueous wetting device as well as the "glue" to bond the cover onto the microfabricated features. The resulted microfluidic device was found to transmit about 50% of the UV light at a wavelength of 210 nanometers.

Example 3

A device made of polydimethylsiloxane (PDMS) was cast containing a 100 micrometer wide separation channel with a section of the channel, called a "bubble", having a vertical dimension of 200 microns. The PDMS device was bonded to a quartz plate with built-in platinum electrodes for use as an electrophoresis device. A supply reservoir was connected to one end and a waste reservoir was connected to the other end of the separation channel. The bubble was aligned with a 200 micron long by 100 micron wide optical detection slit. A standard solution of 400 micromolar para-hydroxycinnamic acid in methanol was injected into the 100 micron-width separation channel filled with a pH 9.3 aqueous borate buffer through a 50 micron-wide cross channel in the T-injection junction, similar to FIG. 1. A potential difference of 3.5 kV was applied between the electrodes in contact with the supply reservoir filled with a pH 9.3 aqueous borate buffer, and in contact with the waste reservoir. Ultraviolet light at a wavelength of 280 nm filtered from light from a deuterium lamp operating at a power of 30 Watts was passed through the slit and through the bubble of the device. A sharp peak of UV absorption with intensity of about 0.02 absorption unit was observed at about one minute after the application of electrophoretic voltage.

What is claimed is:

1. An improved microfluidic system, comprising:
   a microfluidic device which comprises a planar substrate having a first surface and a planar cover having a first surface, the first surface of the cover being bonded to the first surface of the planar substrate, at least one of the substrate or cover being substantially fabricated from a polymeric material comprising a perfluorodimethyldioxole repeating unit or an amorphous fluoropolymer known as Teflon AF®, the device having at least first and second intersecting channels disposed therein at the interface of the bonded surfaces, the channels having interior surfaces being optionally wetted with aqueous and/or organic/aqueous buffers, and having a zeta potential associated therewith, which zeta potential is capable of supporting an electroosmotic mobility of a fluid in said channels of at least $1 \times 10^{-5}$ $cm^2 V^{-1} s^{-1}$, wherein said fluid is a sodium borate buffer having an ionic strength of between about 1 and about 50 millimoles (mM), and a pH of from about 7 to about 9.5, at least one of said at least first and second intersecting channels having at least one cross-sectional dimension in the range of from about 0.1 micrometer to about 1000 micrometers;

at least first, second and third ports disposed at termini of said first channel and at least one terminus of said second channel, whereby said ports are in electrical contact with the fluid in said first and second channels; and an electrical control system for concomitantly applying a voltage to at least two of said at least first, second and third ports, to selectively direct flow of the fluid in said first and second intersecting channels by electroosmotic flow, wherein the improvement comprises spin-coating a layer of polyvinyl alcohol on at least one of the first surfaces to render the surface hydrophilic and to facilitate bonding the two first surfaces.

* * * * *